United States Patent
Bhirud et al.

(10) Patent No.: US 10,703,744 B2
(45) Date of Patent: Jul. 7, 2020

(54) PROCESS FOR PREPARATION OF LULICONAZOLE

(71) Applicant: Glenmark Life Sciences Limited, Solapur (IN)

(72) Inventors: Shekhar Bhaksar Bhirud, Mumbai (IN); Kumar Hari Bhushan, Gurgaon (IN); Sunil Sudhakar Zhope, Pune (IN); Shailesh Govind Ghadigaonkar, Thane (IN); Pardeep Singh, Ropar (IN); Shekhar Ashok Deshmukh, Ahemdnagar (IN); Prem Chand, Navi (IN)

(73) Assignee: GLENMARK LIFE SCIENCES LIMITED, Solapur (IN)

( * ) Notice: Subject to any disclaimer, the term of this patent is extended or adjusted under 35 U.S.C. 154(b) by 0 days.

(21) Appl. No.: 15/533,699

(22) PCT Filed: Dec. 9, 2015

(86) PCT No.: PCT/IB2015/059455
§ 371 (c)(1),
(2) Date: Jun. 7, 2017

(87) PCT Pub. No.: WO2016/092478
PCT Pub. Date: Jun. 16, 2016

(65) Prior Publication Data
US 2017/0362212 A1     Dec. 21, 2017

(30) Foreign Application Priority Data
Dec. 12, 2014  (IN) .................... 3992/MUM/2014

(51) Int. Cl.
*C07D 409/06* (2006.01)
*A61K 31/4178* (2006.01)

(52) U.S. Cl.
CPC ........ *C07D 409/06* (2013.01); *A61K 31/4178* (2013.01); *C07B 2200/13* (2013.01)

(58) Field of Classification Search
CPC .................................................... C07D 409/06
USPC ..................................................... 548/315.1
See application file for complete search history.

(56) References Cited

U.S. PATENT DOCUMENTS

| | | |
|---|---|---|
| 5,900,488 A | 5/1999 | Kodama et al. |
| 9,012,484 B2 | 4/2015 | Masuda et al. |
| 9,050,271 B2 | 6/2015 | Kobayashi et al. |
| 2015/0368233 A1 | 12/2015 | Masuda et al. |

FOREIGN PATENT DOCUMENTS

| | | | | |
|---|---|---|---|---|
| CN | 103012385 A | | 4/2013 | |
| CN | 104151305 A | * | 11/2014 | |
| WO | WO-9702821 A2 | * | 1/1997 | ......... A61K 31/4178 |
| WO | WO-2014041825 A1 | * | 3/2014 | ........... C07D 409/06 |
| WO | WO-2014136282 A1 | * | 9/2014 | ........... C07D 409/06 |

OTHER PUBLICATIONS

English translation of the claims in the Chinese publication CN-104151305-A. (Year: 2014).*
English translation of the description in the Chinese publication CN-104151305-A. (Year: 2014).*

* cited by examiner

*Primary Examiner* — Matthew P Coughlin
*Assistant Examiner* — Sagar Patel
(74) *Attorney, Agent, or Firm* — Blank Rome LLP

(57) ABSTRACT

A process for the preparation of luliconazole and salts thereof is disclosed.

9 Claims, 5 Drawing Sheets

PROCESS FOR PREPARATION OF LULICONAZOLE

This application claims priority under 35 U.S.C. § 371 to International Application No. PCT/IB2015/059455, filed Dec. 9, 2015 which claims the benefit of Indian Provisional Application 3992/MUM/2014 filed Dec. 12, 2014, and entitled "Process for Preparation of Luliconazole", the contents of which are incorporated herein by reference.

PRIORITY

This application claims the benefit of Indian Provisional Application 3992/MUM/2014 filed on Dec. 12, 2014, entitled "Process for Preparation of Luliconazole", the contents of which are incorporated herein by reference.

FIELD OF THE INVENTION

The present invention relates to a process for the preparation of luliconazole and salts thereof.

BACKGROUND OF THE INVENTION

Luliconazole is an antimycotic agent in the azole class. Luliconazole, chemically known as (2E)-2-[(4R)-4-(2,4-dichlorophenyl)-1,3-dithiolan-2-ylidene]-2-imidazol-1-ylacetonitrile, is represented by compound of formula I,

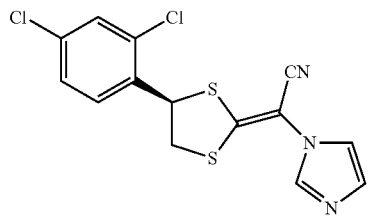

I

Luliconazole is currently marketed in United States under the trade name Luzu cream, 1% contains 1% luliocnazole in a white cream for topical application. Luzu cream, 1% is indicated for the topical treatment of interdigital tinea pedis, tinea cruris, and tinea corporis caused by the organisms *Trichophyton rubrum* and *Epidermophyton floccosum*, in patients 18 years of age and older.

The present invention provides a novel process for preparation of luliconazole which provides a better purity profile and which can be easily performed on industrial scale.

SUMMARY OF THE INVENTION

The present invention provides a process for the purification of luliconazole, a compound of formula I, comprising the steps of

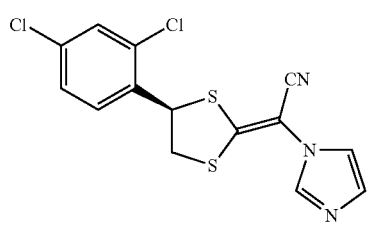

I (i) contacting a mixture comprising luliconazole and the stereoisomer/s thereof in a solvent with an acid to provide a reaction mixture comprising an acid addition salt of luliconazole and optionally acid addition salt of stereoisomer/s of luliconazole;
(ii) separating the acid addition salt of luliconazole from the above reaction mixture; and
(iii) basifying the separated acid addition salt of luliconazole to form luliconazole.

The present invention provides process for the preparation of luliconazole hydrochloride, the compound of formula IV, comprising:

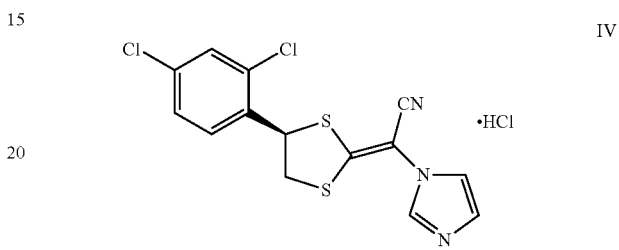

IV a) reacting a compound of formula V with a compound of formula III to obtain the compound of formula I; and

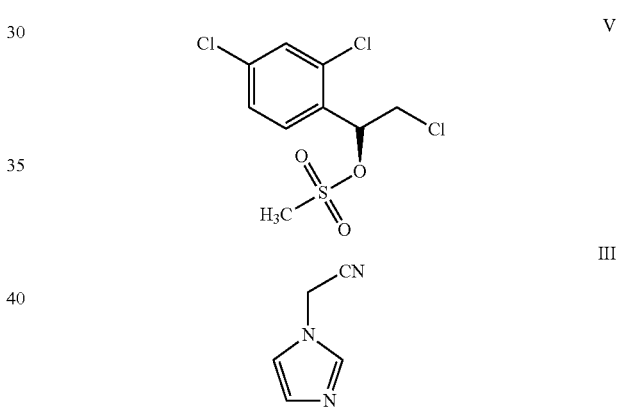

V

III b) reacting the compound of formula I with hydrochloric acid to obtain luliconazole hydrochloride, the compound of formula IV.

The present invention provides a process for the preparation of crystalline luliconazole, the compound of formula I comprising crystallizing luliconazole from a solvent selected from the group consisting of ketone, nitrile, water, sulfoxides, cyclohexane, and mixtures thereof.

The present invention provides crystalline luliconazole hydrochloride.

The present invention provides use of luliconazole hydrochloride in preparation of luliconazole.

DETAILED DESCRIPTION OF THE INVENTION

Figure 1:
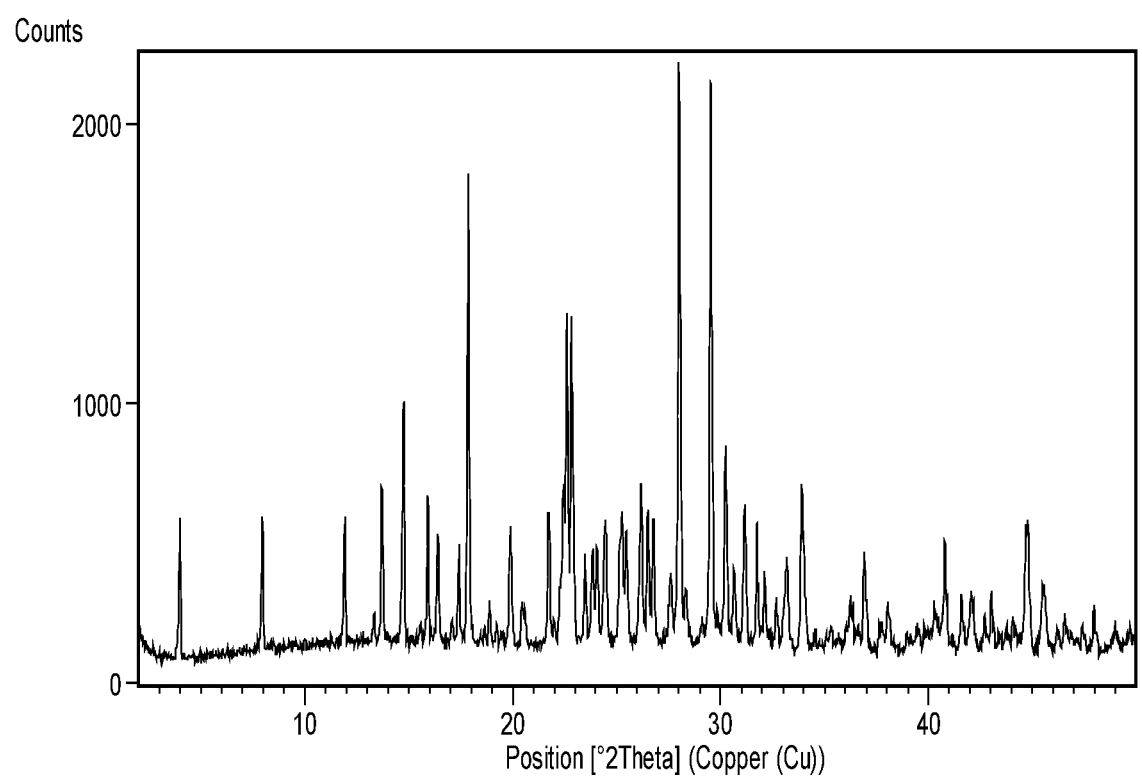
FIG. 1: XRD pattern of luliconazole hydrochloride according to example 8.

In one embodiment, the present invention provides a process for the purification of luliconazole, a compound of formula I, comprising the steps of

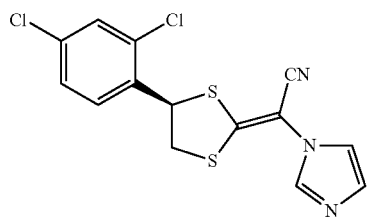

I (i) contacting a mixture comprising luliconazole and the stereoisomer/s thereof in a solvent with an acid to provide a reaction mixture comprising an acid addition salt of luliconazole and optionally acid addition salt of stereoisomer/s of luliconazole;
(ii) separating the acid addition salt of luliconazole from the above reaction mixture; and
(iii) basifying the separated acid addition salt of luliconazole to form luliconazole.

The term "stereoisomers" refers to compounds which have identical chemical constitution, but differ with regard to the arrangement of the atoms or groups in space.

In one embodiment, in a) of the above process the stereoisomers of luliconazole are the Z and SE isomer of luliconazole represented by the compound of formula VIII and IX respectively.

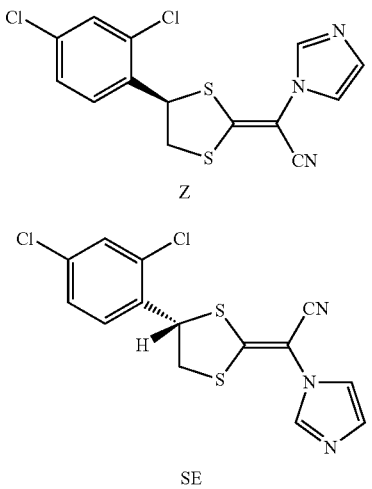

In one embodiment the present invention provides luliconazole wherein the content of Z or SE isomer of luliconazole, the compound of formula VIII and IX respectively, in the obtained luliconazole is less than 0.5% w/w with respect to luliconazole as measured by HPLC.

As used herein the term "contacting" refers to treating, suspending or slurrying the mixture of luliconazole and the stereoisomer/s thereof.

In one embodiment, in i) of the above process involving contacting a mixture comprising luliconazole and the stereoisomer/s thereof in a solvent with an acid provides a reaction mixture comprising an acid addition salt of luliconazole and acid addition salt of stereoisomer/s of luliconazole.

In one embodiment, in i) of the above process involving contacting a mixture comprising luliconazole and the stereoisomer/s thereof in a solvent with an acid provides a reaction mixture comprising an acid addition salt of luliconazole and stereoisomer/s of luliconazole.

In one embodiment, in i) of the above process involving contacting a mixture comprising luliconazole and the stereoisomer/s thereof in a solvent with an acid provides a reaction mixture comprising an acid addition salt of luliconazole, stereoisomers of luliconazole and acid addition salt of stereoisomer/s of luliconazole.

In one embodiment, in i) of the above process the acid is an organic or an inorganic acid.

In one embodiment, in i) of the above process organic acid used to provide an acid addition salt may include an acid such as formic acid, acetic acid, citric acid, tartaric acid, bitartaric acid, benzoic acid, lactic acid, malic acid, fumaric acid, succinic acid, gluconic acid, pamoic acid, methanesulfonic acid, benzenesulfonic acid and the like and the inorganic acid used, to provide an acid addition salt, may include an acid such as hydrochloric acid, hydrobromic acid, hydroiodic acid, nitric acid, phosphoric acid, sulfuric acid, trifluoroacetic acid, and the like.

In one embodiment, the inorganic acid is hydrochloric acid.

In one embodiment, the acid addition salt of luliconazole is luliconazole hydrochloride.

A suitable solvent for step i) may be selected from, but is not limited to alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; water or mixtures thereof.

In one embodiment, in ii) of the above process the separation is carried out by steps comprising:
(Gi) selectively separating the acid addition salt of luliconazole from the reaction mixture comprising an acid addition salt of luliconazole and optionally acid addition salt of stereoisomer/s of luliconazole based on their differential solubility in solvents; and
(Gii) isolating the acid addition salt of luliconazole.

As used herein the term "differential solubility" refers to the solubility wherein either the acid addition salt of luliconazole is selectively soluble while the stereoisomers of luliconazole or the acid addition salt of stereoisomers of luliconazole are insoluble in a suitable solvent. The separation occurs due to difference in degree of solubility between the acid addition salt of luliconazole and that of stereoisomers of luliconazole or acid addition salt of stereoisomers of luliconazole in a particular solvent or solvent system.

Thus separation can be achieved faster in a particular solvent or solvent system by virtue of difference in degree of solubility of the compounds to be separated.

In embodiment, in (Gi) of the above process, the acid addition salt of luliconazole is selectively separated by addition of an anti-solvent to the mixture comprising acid addition salt of luliconazole and optionally acid addition salt of stereoisomers of luliconazole.

In one embodiment, in (Gi) of the above process, acid addition salt of luliconazole is selectively separated from the mixture comprising acid addition salt of luliconazole and optionally acid addition salt of stereoisomers of luliconazole whereby the acid addition salt of luliconazole is insoluble in the solvent.

The solvent or the anti-solvent in which the acid addition salt of luliconazole is insoluble and the acid addition salts of stereoisomers or the stereoisomers of luliconazole are soluble may be selected from, but is not limited to alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; water or mixtures thereof.

In one embodiment, the acid addition salt of luliconazole is selectively separated from the mixture comprising acid addition salt of luliconazole and optionally acid addition salt of stereoisomers of luliconazole by a process comprising:

Ji) removing solvent from the mixture comprising acid addition salt of luliconazole and optionally acid addition salt of stereoisomers of luliconazole; and Jii) optionally, adding a second solvent to step 'Ji'.

In one embodiment, Ji) of the above process involves partial or complete removal of the solvent from the mixture comprising acid addition salt of luliconazole and optionally acid addition salt of stereoisomers of luliconazole.

In one embodiment, the removal of solvent is carried out by methods selected from the group consisting of filtration, distillation, evaporation, centrifugation, spray drying and freeze drying.

In one embodiment, Jii) of the above process involves optional addition of a second solvent to the mixture comprising acid addition salt of luliconazole and optionally acid addition salt of stereoisomers of luliconazole.

The addition of a second solvent is carried out, optionally if the solvent is completely removed in the above step Ji).

In one embodiment, the salt of luliconazole is selectively separated by completely removing the solvent from the mixture comprising acid addition salt of luliconazole and optionally acid addition salt of stereoisomers of luliconazole and addition of a second solvent to the resultant mixture comprising acid addition salt of luliconazole and optionally acid addition salt of stereoisomers of luliconazole to obtain slurry.

In one embodiment, in the obtained slurry the acid addition salt of luliconazole remains insoluble and the acid addition salt of stereoisomers or stereoisomers of luliconazole remains in solution.

The second solvent in which the salt of luliconazole is insoluble may be selected from, but is not limited to alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; water or mixtures thereof.

In one embodiment, in Gii) of the above process acid addition salt of luliconazole is selectively separated from the above slurry by methods known in the art such as filtration, centrifugation, spray drying and the like.

Thus in the above defined process the acid addition salt of luliconazole is separated from the mixture comprising acid addition salt of luliconazole and optionally acid addition salt of stereoisomers of luliconazole based on their differential solubility.

In one embodiment, it is surprisingly noted that there is an essential difference in the solubility of the acid addition salt of luliconazole from that of the stereoisomers of luliconazole and the acid additions salt of stereoisomers of luliconazole. This difference in solubility enhances the purity of the acid addition salt of luliconazole when isolated from a mixture comprising acid addition salt of luliconazole optionally with acid additions salt of stereoisomers of luliconazole from the solvent.

In one embodiment, the solubility difference provides a faster and easier separation of the acid addition salt of luliconazole from the mixture of acid addition salt of luliconazole optionally with acid additions salt of stereoisomers of luliconazole.

In one embodiment, the acid addition salt of luliconazole may be soluble in a solvent at reflux temperature or at low temperature and the acid addition salt of stereoisomer/s and stereoisomer/s of luliconazole may be insoluble.

In one embodiment, the process of separation by differential solubility involves selection of the solvent, based on the determination of the degree of solubility of the acid addition salt of luliconazole and the degree of insolubility of the stereoisomer/s of luliconazole or the acid addition salt of stereoisomer/s of luliconazole in a particular solvent.

In one embodiment, the acid addition salt of stereoisomer of luliconazole is converted to the acid addition salt of luliconazole.

In one embodiment, the stereoisomers of luliconazole are converted to luliconazole by methods such as heating in a solvent. The heating may be carried out in presence or absence of an acid or a base.

In one embodiment, the stereoisomer of luliconazole hydrochloride is converted to luliconazole or luliconazole hydrochloride In one embodiment, in iii) of the above process the acid addition salt of luliconazole is subjected to basification to form luliconazole.

The suitable bases may be selected from, but not limited to ammonia, hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like.

The present invention provides a process for the purification of luliconazole, a compound of formula I, comprising the steps of

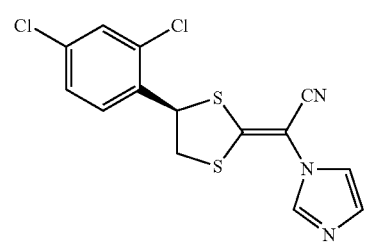

I i) contacting a mixture comprising acid addition salt of luliconazole and stereoisomer/s thereof in a solvent with hydrochloric acid to provide a reaction mixture comprising luliconazole hydrochloride and optionally stereoisomer/s of luliconazole;

ii) separating the luliconazole hydrochloride from the above obtained reaction mixture; and iii) basifying the separated luliconazole hydrochloride to form luliconazole.

In one embodiment, the present invention provides a process for the purification of luliconazole comprising the steps of contacting a mixture comprising acid addition salt of luliconazole and optionally acid addition salt of stereoisomer/s of luliconazole with hydrochloric acid in ethyl acetate to provide a reaction mixture comprising luliconazole hydrochloride and optionally the hydrochloride salt of stereoisomers of luliconazole. The addition of hydrochloric acid may be by purging dry hydrochloride gas, using aqueous hydrochloric acid or by addition of hydrochloric acid dissolved in ethyl acetate. The addition is carried out at a temperature of about 0° C. to about reflux temperature of the solvent. Preferably, the addition is carried out at about 10-20° C.

In one embodiment, luliconazole hydrochloride is selectively separated by removing the solvent from the mixture comprising luliconazole hydrochloride and optionally stereoisomers of luliconazole by distillation and addition of acetone to obtain a slurry wherein luliconazole hydrochloride is insoluble and the stereoisomers of luliconazole or the stereoisomers of luliconazole hydrochloride is soluble. Luliconazole hydrochloride is isolated by filtration.

In one embodiment crystalline luliconazole is prepared by a process comprising
a) subjecting slurry of luliconazole in a solvent to elevated temperature to obtain a solution; and
b) cooling the solution to obtain crystalline luliconazole.

In one embodiment crystalline luliconazole is prepared by process comprising
a) subjecting a slurry of luliconazole in a solvent to elevated temperature to obtain a solution; and
b) adding an anti-solvent to obtain crystalline luliconazole.

The suitable solvent may be selected from, but is not limited to alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; nitrile such as acetonitrile, water or mixtures thereof.

In one embodiment, the anti-solvent may be selected from the group consisting of methanol, hexane, water and mixtures thereof.

In one embodiment, the solvent is ethyl acetate and anti-solvent is hexane. The ratio of ethyl acetate to hexane may be in the range of 1:5 to 5:1.

In one embodiment, luliconazole is crystallized from acetone.

In one embodiment, luliconazole is crystallized from a mixture of acetonitrile and water.

Figure 4:
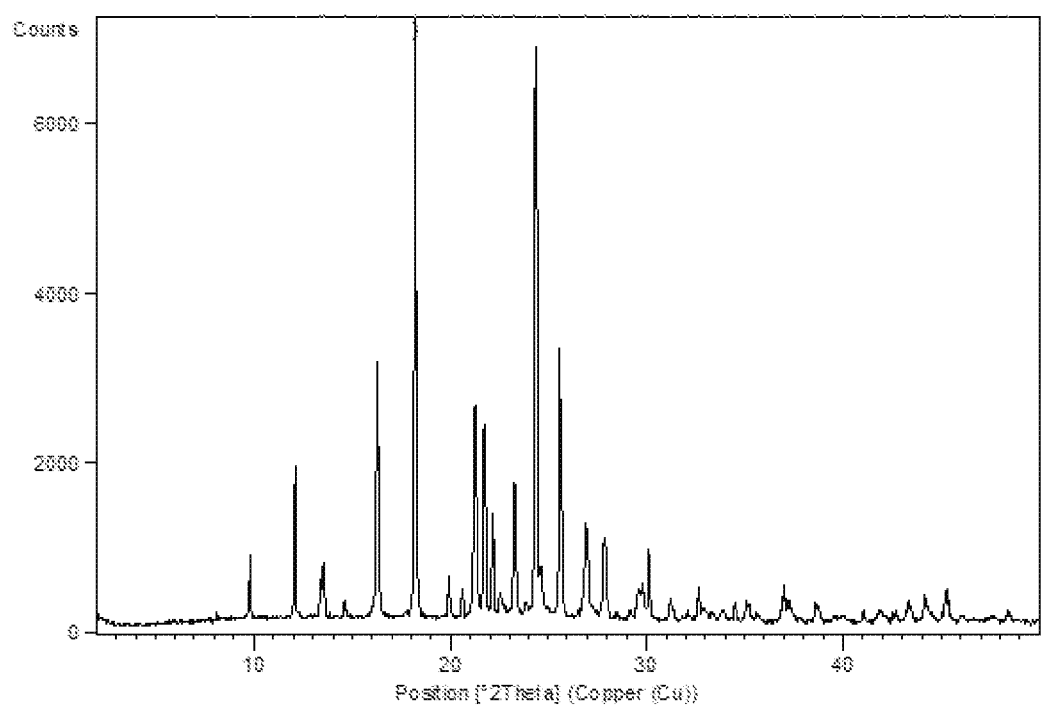
FIG. 4: XRD pattern of luliconazole according to example 17.
Figure 5:
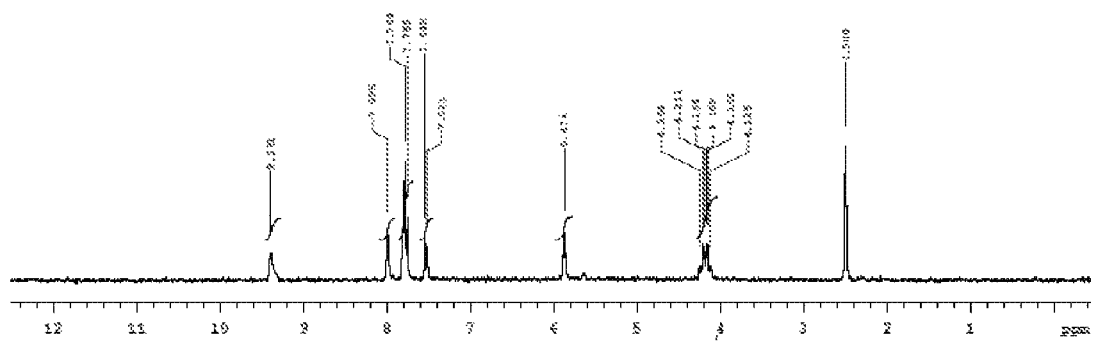
FIG. 5 is a $^1$H NMR of luliconazole hydrochloride according to Example 8.

In one embodiment, the present invention provides luliconazole characterized by X-ray diffraction (XRD) spectrum which is substantially in accordance with FIG. 4.

In one embodiment, the present invention provides luliconazole characterized by Differential Scanning calorimetric (DSC) thermogram having endothermic peak at about 152.03±1° C.

In one embodiment, the present invention provides luliconazole characterized by Thermogravimetric Analysis (TGA) thermogram showing weight loss of about 0.1484% determined over the temp. up to 100° C. and heating rate 10° C./min In one embodiment, the present invention provides luliconazole with a chemical purity of at least 99% w/w and a chiral purity of at least 99% w/w as measured by HPLC.

In one embodiment, the present invention provides use of luliconazole hydrochloride in preparation of luliconazole.

In one embodiment, the present invention provides crystalline luliconazole hydrochloride.

In one embodiment the present invention provides crystalline luliconazole hydrochloride wherein the content of Z or SE isomer of luliconazole hydrochloride, the compound of formula VI and VII respectively, is less than 0.5% w/w with respect to luliconazole hydrochloride as measured by HPLC.

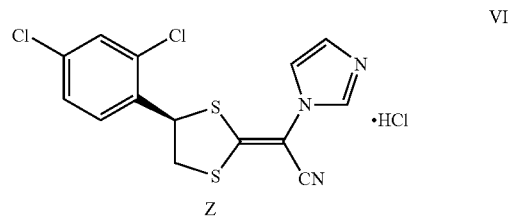

Z

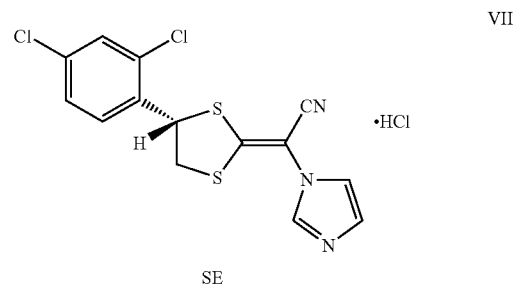

SE

In one embodiment, the present invention provides luliconazole hydrochloride characterized by X-ray diffraction (XRD) spectrum which is substantially in accordance with FIG. 1.

In one embodiment, the present invention provides luliconazole hydrochloride characterized by X-ray diffraction (XRD) spectrum having peak reflections at about 4.0, 8.0, 11.9, 15.9 and 17.9±0.2 degrees 2 theta.

In one embodiment, the present invention provides luliconazole hydrochloride characterized by Differential Scanning calorimetric (DSC) thermogram having endothermic peak at about 210.15° C.±1° C.

In one embodiment, the present invention provides luliconazole hydrochloride characterized by Differential Scanning calorimetric (DSC) thermogram having endothermic peak at about 212.31° C.±1° C.

In one embodiment, the present invention provides luliconazole hydrochloride characterized by Differential Scanning calorimetric (DSC) thermogram having endothermic peak at about 217.15° C.±1° C.

Figure 2:
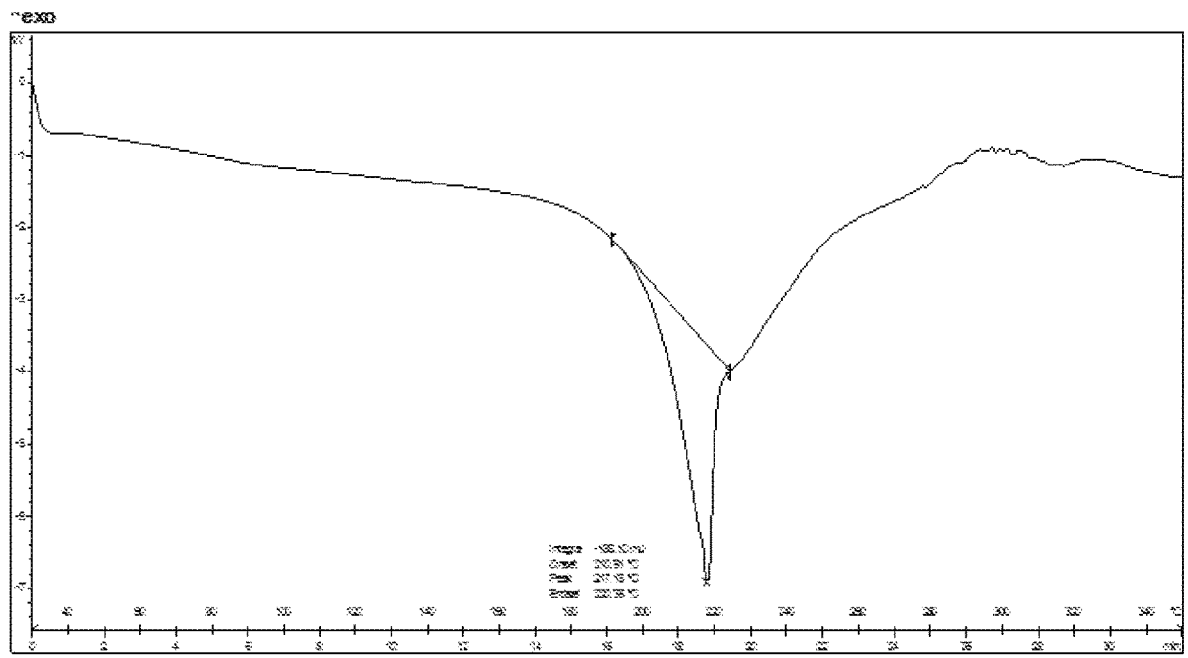
FIG. 2: DSC diffractogram of luliconazole hydrochloride, according to example 8.

In one embodiment, the present invention provides luliconazole hydrochloride characterized by Differential Scanning calorimetric (DSC) thermogram which is substantially in accordance with FIG. 2.

In one embodiment, the present invention provides luliconazole hydrochloride characterized by Thermogravimetric Analysis (TGA) thermogram, showing a weight loss of about 0.30 over the temperature up to 100° C. and heating rate 10° C./min or showing a weight loss of about 2.718% determined over the temperature up to 150° C. and heating rate 10° C./min.

In one embodiment, the present invention provides luliconazole hydrochloride characterized by Thermogravimetric Analysis (TGA) thermogram, showing a weight loss of about 0.44% determined over the temperature up to 100° C. and heating rate 10° C./min or showing a weight loss of about 3.454% determined over the temperature up to 150° C. and heating rate 10° C./min.

In one embodiment, the present invention provides luliconazole hydrochloride characterized by Thermogravimetric Analysis (TGA) thermogram, showing a weight loss of about 0.27% determined over the temperature up to 100° C. and heating rate 10° C./min or showing a weight loss of about 2.4722% determined over the temperature up to 150° C. and heating rate 10° C./min.

Figure 3:
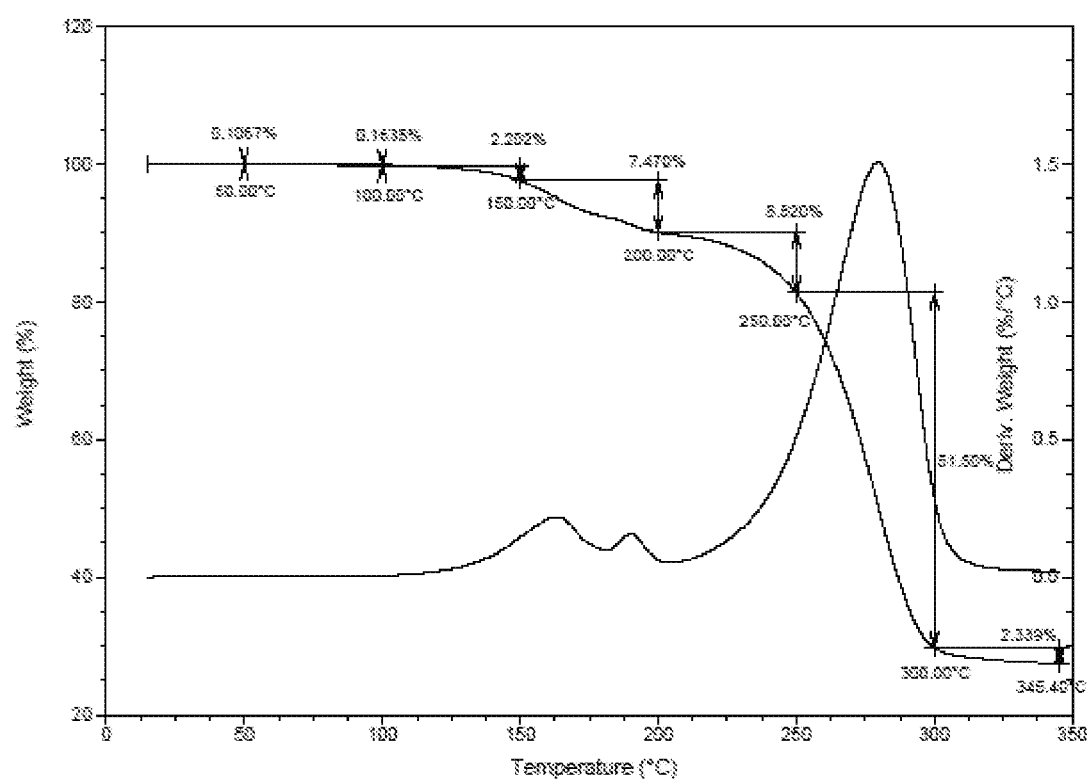
FIG. 3: TGA thermogram of luliconazole hydrochloride, according to example 8.

In one embodiment, the present invention provides luliconazole hydrochloride characterized by Thermogravimetric Analysis (TGA) thermogram which is substantially in accordance with FIG. 3.

In one embodiment, the present invention provides luliconazole hydrochloride characterized by 1HNMR having peaks at 4.12, 4.15, 4.16, 4.19, 4.21, 4.25, 5.87, 7.52, 7.54, 7.75, 7.78, 7.99, and 9.39 (300 MHz, DMSO $d_6$).

In one embodiment, the present invention provides a process for the preparation of luliconazole hydrochloride, the compound of formula IV, comprising:

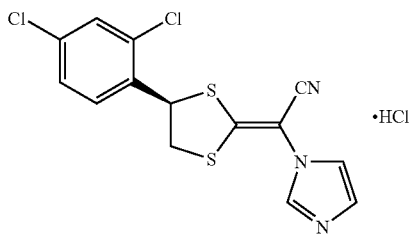

IV a) reacting a compound of formula V with a compound of formula III to obtain the compound of formula I; and

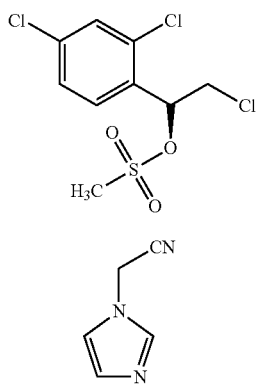

V

III b) reacting the compound of formula I with hydrochloric acid to obtain luliconazole hydrochloride, the compound of formula IV.

In one embodiment, in a) of the above process the compound of formula V is reacted with a compound of formula III in the presence of a solvent.

In one embodiment, the compound of formula III is reacted with a base in a solvent to form an intermediate which is reacted with the compound of formula V to obtain the compound of formula I.

A suitable solvent may be selected from, but is not limited to alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; sulfoxides such as dimethyl sulfoxide; nitriles such as acetonitrile, halogenated solvents such as methylene dichloride, ethylene dichloride, water or mixtures thereof.

A suitable base may be an inorganic base. The inorganic base may be selected from the group consisting of hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like.

In one embodiment, the above reaction is carried out at a temperature of about 20-25° C.

In one embodiment, the compound of formula I is obtained by reacting the compound of formula V with the compound of formula III in the presence of a base in a solvent.

In one embodiment, reaction transpires over a period of about 1 hr to 7 hr.

In one embodiment, in b) of the above process the compound of formula I is reacted with hydrochloric acid to obtain luliconazole hydrochloride, the compound of formula IV.

In one embodiment, in b) of the above process, the reaction is carried out at a temperature of about 0-25° C. The reaction transpires over a period of about 30 min to about 5 hours.

The solvent may be selected from the group consisting of alcohols such as methanol, ethanol, n-propanol, 2-propanol; esters such as ethyl acetate, butyl acetate, isopropyl acetate; hydrocarbons such as toluene, cyclohexane, xylene; ethers such as diethyl ether, di-isopropyl ether; ketones such as acetone, methyl ethyl ketone, methyl isobutyl ketone; sulfoxides such as dimethyl sulfoxide; nitriles such as acetonitrile, halogenated solvents such as methylene dichloride, ethylene dichloride, water or mixtures thereof.

In one embodiment, the compound of formula V is crystallized in a suitable solvent.

The compound of formula V may be crystallised in a solvent selected from the group consisting of alcohols such as isopropyl alcohol, methanol, ethanol, and the like.

In one embodiment, the compound of formula III is reacted with potassium hydroxide in dimethyl sulfoxide to obtain a mixture. The reaction mixture is then added to the compound of formula V to form luliconazole, the compound of formula I.

The luliconazole thus formed is converted to luliconazole hydrochloride by process as disclosed above.

In one embodiment, the present invention provides process for the preparation of crystalline luliconazole, the compound of formula I comprising crystallizing luliconazole from a solvent selected from the group consisting of ketone, nitrile, water, sulfoxides, cyclohexane, and mixtures thereof.

In one embodiment, the present invention provides use of luliconazole hydrochloride in preparation of luliconazole with a chemical purity of at least 99% w/w and a chiral purity of at least 99% w/w as measured by HPLC.

In one embodiment, the present invention provides a process for the preparation of the compound of formula V by a process as depicted schematically:

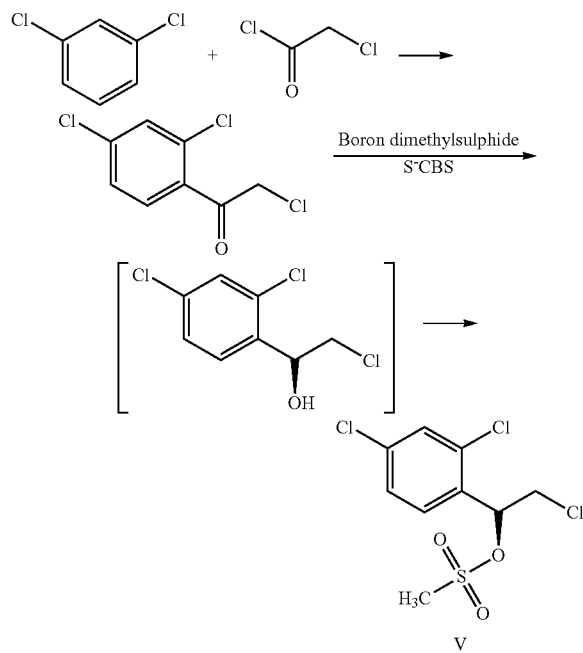

V

In one embodiment, the compound of formula V is prepared by reacting 1,3-dichlorobenzene with chloroacetyl chloride in the presence of a lewis acid to obtain a keto intermediate. The keto intermediate is reacted with S-(–)-2-methyl-CBS-oxazaborolidine to form the S-isomer of hydroxy intermediate, which is further reacted with suitable halogenating agent such as thionyl chloride, phosphorous oxychloride and the like or an activating agent such as methane sulfonyl chloride, toluene sulfonyl chloride and the like to obtain the compound of formula V.

In one embodiment, the compound of formula V is crystallised using isopropyl alcohol.

In one embodiment, the present invention a provides process for the preparation of the compound of formula III by a process as depicted schematically:

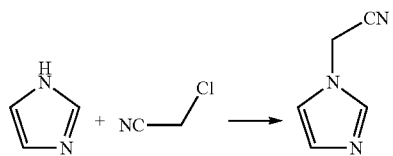

In one embodiment, the compound of formula III is prepared by reacting imidazole with chloroacetonitrile in the presence of a suitable base and a solvent.

In one embodiment, the suitable base may be selected from an organic base such as alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like or an inorganic base such as triethyl amine, trimethyl amine, diisopropyl ethylamine, dimethyl amino pyridine, picoline, dimethyl amino pyridine and pyridine and the like.

In one embodiment, the present invention provides luliconazole free of below impurity

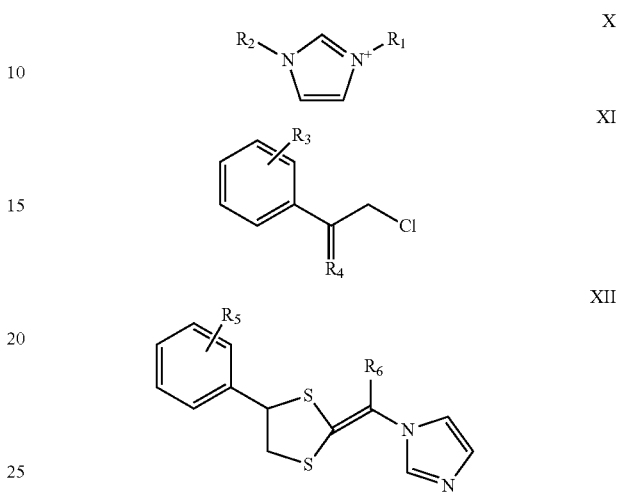

wherein $R_1$=H or alkyl cyanide and $R_2$=H, CH2COOH, —CH2CONH2, alkyl cyanide $R_3$ is H or chloro substituent at one or more positions on the phenyl ring; $R_4$ is H, O, hydroxy, methanesulfonyloxy and ═══ is either a double bond or a single bond. $R_5$ is a chloro substituent at one or more positions on the phenyl ring; $R_6$ is cyano or amide group, with the proviso that $R_6$ is not 2,4-dichloro substituent.

In one embodiment, the present invention provides luliconazole free of below impurity

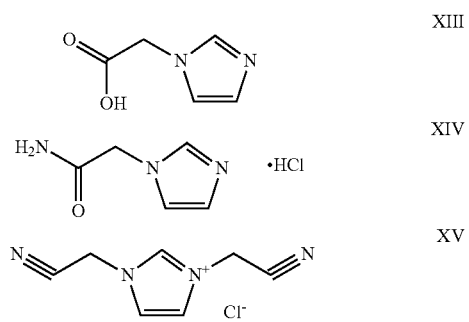

In one embodiment, the present invention provides luliconazole free of any of the below listed racemic or stereoisomer impurity

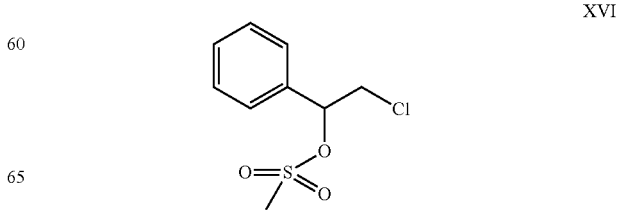

-continued
XVII
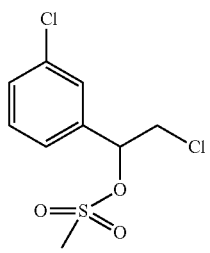
XVIII
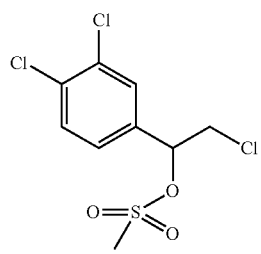
XIX
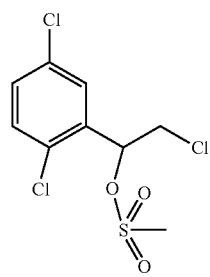
XX
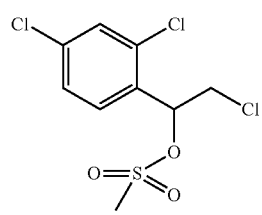
XXI
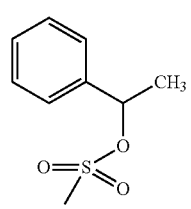
XXII
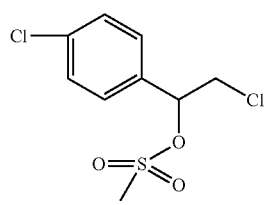
-continued
XXIII
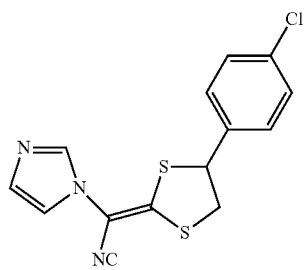
XXIV
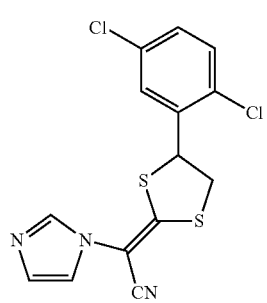
XXV
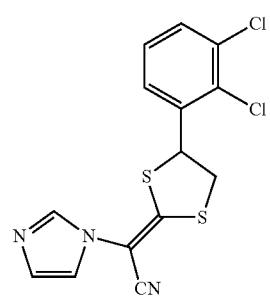
XVI
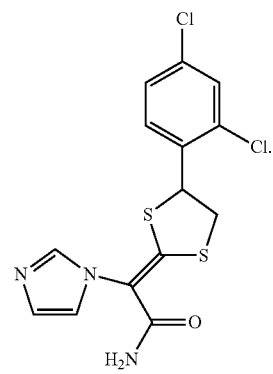
In one embodiment, the present invention provides luliconazole free of below stereo isomers:
VIII
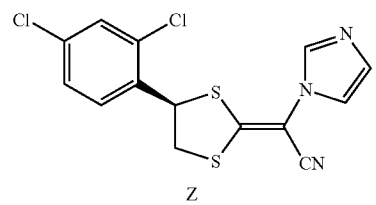

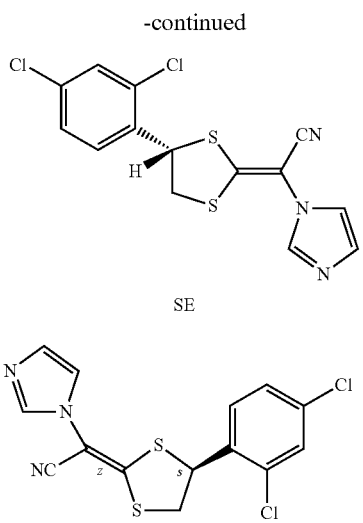

In one embodiment, the present invention provides a method of assessing the purity of luliconazole by HPLC comprising the steps of:
a) providing a standard solution of the impurity; and
b) using the solution as a reference marker to determine the level of impurity.

In one embodiment, the impurity is selected from III, V, XIII, XIV, XV, XX, XXI XXII, XXIII, XXIV, XXV, XVI, VIII, IX, XIII, VIII, IX and XIII In one embodiment, the present invention provides pharmaceutical compositions comprising luliconazole or salt thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns.

In one embodiment, the present invention provides luliconazole or salt obtained by the processes herein described having $D_{90}$ particle size of less than about 16 microns and $D_{50}$ particle size of less than about 8 microns.

The particle size disclosed here can be obtained by, for example, any milling, grinding, micronizing or other particle size reduction method known in the art to bring the solid state luliconazole or salt into any of the foregoing desired particle size range.

The present invention provides luliconazole as characterized and analyzed by following techniques:
A] X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator [1]; Scanning Mode; Active length (2Theta)=2.122°; generator 45 KV; tube current 40 mAmp. The samples were scanned in the full 2θ range of 2-50° with a "time-per-step" 50 seconds.
B] PSD: Particle size analysis was performed on Malvern Mastersizer 2000 with Sample handling unit 'Hydro2000S (A)' using 0.5% w/v solution of tween 80 in water.
C] DSC (Mettler Toledo 822e): Temperature range is "30° C. to 350° C." and heating rate is 10° C./minute.
D] Instrumental settings for TGA: Instrument Name: TGA Q 500; Method: 5-8 mg of sample was taken in platinum pan and heated at 10° C./minute from room temperature to 350° C.
E] Instrumental settings for NMR: Proton NMR spectra were recorded in DMSO-$d_6$ using NMR instrument-Varian 300 MHZ
F] Instrumental settings for HPLC for chiral purity: Reagents and Solvents: n-hexane, ethanol, Isopropyl alcohol. Column: Diacel Chiralpak, AD-H, 250×4.6 mm, 5μ.column temperature: 30° C., Mobile Phase:n-Hexane, ethanol, Isopropyl alcohol, Diluent: n-Hexane, ethanol, flow rate: 1.0 mL/min, Detection US210 nm, Injection volume:20 μL, Run times: 50 min.
G] Instrumental settings for HPLC for chemical purity: column: Inertsil ODS 3V, 250×4.6 mm, 5μ column temperature: 40° C., Mobile Phase:Mobile Phase A:Buffer:Acetonitrile, Buffer:1.0 mL of perchloric acid in 1000 ml of water, Mobile Phase B: Buffer:Acetonitrile:Methanol, Diluent:water: Acetonitrile, flow rate: 1.0 mL/min, Detection US210 nm, Injection volume:20 μL The following examples are provided to enable one skilled in the art to practice the invention and are merely illustrative of the invention. The examples should not be read as limiting the scope of the invention.

EXAMPLES

Example 1: Preparation of 2-chloro-1-(2,4-dichlorophenyl)ethanone 1,3-Dichlorobenzene was added to a cooled reaction mixture containing chloroacetyl chloride and aluminum chloride. The reaction mass was stirred for 8 hrs and quenched into water and ethyl acetate. Layers were separated and ethyl acetate layer was distilled. To this isopropyl alcohol was added, heated and maintained for 30 min. The reaction mass was cooled and maintained for 120 min and filtered to obtain the product, 2-chloro-1-(2,4-dichlorophenyl)ethanone.

Example 2: Preparation of 2-Chloro-1-(2,4-Dichlorophenyl)Ethanone

To a cooled mixture of methylene dichloride and aluminum chloride were added chloroacetyl chloride and 1,3-Dichlorobenzene. The reaction mass was stirred for 8 hrs and quenched into a methylene dichloride and water. The methylene dichloride layer was distilled under vacuum. The product was crystallised in isopropyl alcohol to obtain 2-chloro-1-(2,4-dichlorophenyl)ethanone. HPLC purity>98%

Example 3: Preparation of (αS)2,4-Dichloro-α-(Chloromethyl)-Benzene Methanol Methane Sulfonate A mixture of methylene dichloride and S-(−)-2-methyl-CBS-oxazaborolidine solution in 1.0 M toluene catalyst was heated and boron dimethyl sulphide solution was added. The reaction mass was stirred for 60 min. A solution of 2-chloro-1-(2,4-dichlorophenyl) ethanone in methylene dichloride was added to the above reaction mass. The reaction mass was cooled and methanol was added followed by water and the layers were separated. The methylene dichloride layer was distilled partially and to this triethyl amine was added. The reaction mass was cooled to a temperature of about 10-15° C. and methane sulphonyl chloride was added. The reaction mixture was acidified using conc HCl solution. The methylene dichloride layer was separated and distilled. The product was crystallised in isopropyl alcohol. Chiral HPLC purity>99.0%.

Example 3a)

The above reaction was repeated in tetrahydrofuran as solvent. Chiral HPLC purity—98.34%

Example 4: Preparation of 1H-Imidazole-1-Acetonitrile

To a mixture of ethyl acetate and imidazole was added sodium carbonate followed by chloroacetonitrile. The reaction mixture was heated and maintained for 16 hrs and then cooled and filtered. The filtrate was distilled under vacuum and to this xylene was added and distilled under vacuum. Methylene dichloride was added to the residue and stirred for an hour. The reaction mass was filtered. The filtrate was distilled to obtain product. HPLC Purity: 97.15%.

Example 5: Preparation of 1H-Imidazole-1-Acetonitrile

To a mixture of toluene and imidazole was added triethyl amine followed by chloroacetonitrile. The reaction mixture was heated and maintained for 7 to 8 hrs. The reaction mass was cooled and the toluene layer was separated. To the reaction mass methylene dichloride was added, stirred and filtered. The filtrate was distilled under vacuum. To the residue tetrahydrofuran was added and the reaction mixture is further distilled to obtain the title product. The product thus obtained was recrystallized in isopropyl alcohol. HPLC purity>99.0% Chiral purity>99.0%

Example 6: Preparation of 1H-Imidazole-1-Acetonitrile

To a mixture of ethyl acetate and imidazole were added chloroacetonitrile and potassium carbonate. The reaction mass was heated and maintained for 6 hrs. The reaction mass was filtered and the filtrate was distilled under vacuum and to the residue thus obtained tetrahydrofuran was added. This was further stirred at elevated temperature and filtered. The filtrate was distilled under vacuum to obtain title product. HPLC purity—90.75%

Example 7: Preparation of 1H-Imidazole-1-Acetonitrile

To a mixture of ethyl acetate and imidazole were added chloroacetonitrile and sodium carbonate. The reaction mixture was heated to 70-80° C. and maintained for 6 hrs. The reaction mixture was filtered and the filtrate was distilled under vacuum to obtain an oily residue. To the residue was added methylene dichloride. The reaction mixture was stirred and filtered through hyflo bed and the filtrate was distilled under vacuum to obtain title product. HPLC purity: 89.92%

The product was further purified by dissolving in methylene dichloride and subjecting to charcoal treatment, the reaction mass was stirred for next 2-3 hours and filtered through hyflo bed. The filtrate was distilled under reduced vacuum to get 1H-imidazole-1-acetonitrile with HPLC purity>98.0%

Example 8: Preparation of Luliconazole

To a mixture of 1H-imidazole-1-acetonitrile (compound III) in dimethyl sulphoxide and carbon disulphide was added powered potassium hydroxide to obtain potassium salt of α-(dimercaptomethylene)-1H-Imidazole-1-acetonitrile. In another flask dimethyl sulphoxide and (αS) 2,4-dichloro-α-(chloromethyl)-benzene methanol methanesulfonate (compound V) were added, stirred and cooled. To this reaction mixture was added above prepared potassium salt of α-(dimercaptomethylene)-1H-Imidazole-1-acetonitrile. The reaction mixture was stirred and quenched in water. The reaction mixture was extracted with ethyl acetate and washed with water and brine. To the ethyl acetate layer was added a solution of ethyl acetate.HCl, stirred. The reaction mixture was distilled to obtain solid. The solid was stirred in acetone, filtered and dried to get luliconazole hydrochloride. Chiral purity: 95.0%, HPLC Purity>99.5%. Z:isomer content: 4.34, other undesired isomer content: 0.65

NMR of luliconazole Hydrochloride: 1H NMR (300 MHz, DMSO $d_6$) having peaks at 4.12, 4.15, 4.16, 4.19, 4.21, 4.25, 5.87, 7.52, 7.54, 7.75, 7.78, 7.99, and 9.39.

chloride content in luliconazole hydrochloride:9.6%

| XRD table of luliconazole hydrochloride: | | |
|---|---|---|
| Pos. [°2Th.] | d-spacing [Å] | Rel. Int. [%] |
| 4.00 | 22.06 | 24.32 |
| 8.00 | 11.10 | 23.51 |
| 11.94 | 7.41 | 22.70 |
| 13.32 | 6.65 | 4.79 |
| 13.73 | 6.45 | 26.78 |
| 14.75 | 6.01 | 41.88 |
| 15.55 | 5.70 | 3.43 |
| 15.92 | 5.57 | 26.12 |
| 16.41 | 5.40 | 19.25 |
| 17.09 | 5.19 | 3.99 |
| 17.42 | 5.09 | 17.19 |
| 17.9 | 4.96 | 81.12 |
| 18.89 | 4.70 | 7.67 |
| 19.23 | 4.62 | 3.60 |
| 19.87 | 4.47 | 17.84 |
| 20.45 | 4.34 | 6.89 |
| 21.73 | 4.09 | 22.95 |
| 22.45 | 3.96 | 27.80 |
| 22.61 | 3.93 | 57.30 |
| 22.82 | 3.90 | 55.71 |
| 23.48 | 3.79 | 15.24 |
| 23.83 | 3.73 | 5.46 |
| 24.05 | 3.70 | 16.49 |
| 24.50 | 3.63 | 18.61 |
| 25.27 | 3.52 | 22.97 |
| 25.47 | 3.50 | 19.32 |
| 26.17 | 3.41 | 27.40 |
| 26.49 | 3.37 | 22.72 |
| 26.75 | 3.33 | 21.57 |
| 27.60 | 3.23 | 11.79 |
| 28.00 | 3.19 | 100.0 |
| 28.34 | 3.15 | 8.86 |
| 29.52 | 3.03 | 97.72 |
| 30.24 | 2.96 | 34.45 |
| 30.64 | 2.92 | 12.05 |
| 31.15 | 2.87 | 24.17 |
| 31.73 | 2.82 | 21.73 |
| 32.11 | 2.79 | 13.40 |
| 32.67 | 2.74 | 8.83 |
| 33.18 | 2.70 | 15.60 |
| 33.90 | 2.64 | 27.83 |
| 35.32 | 2.54 | 3.69 |
| 36.23 | 2.48 | 7.52 |
| 36.91 | 2.44 | 16.72 |
| 37.64 | 2.39 | 3.50 |
| 38.06 | 2.36 | 7.51 |
| 39.01 | 2.31 | 2.21 |

-continued

XRD table of luliconazole hydrochloride:

| Pos. [°2Th.] | d-spacing [Å] | Rel. Int. [%] |
|---|---|---|
| 40.28 | 2.24 | 6.85 |
| 40.78 | 2.21 | 18.51 | luliconazole hydrochloride was stirred in water and basified to a pH of 8.0 to 9.0 using aqueous ammonia. The reaction mass was maintained, filtered and dried to obtain luliconazole. Luliconazole is crystallised in acetonitrile and water mixture. Chiral purity: 99.94%, HPLC Purity > 99.97%. Z: isomer content: 0.02%, other undesired isomer content: 0.0.04%.

Example 9: Purification of Luliconazole Hydrochloride in Acetone 40 ml acetone was added to 2 g luliconazole hydrochloride and the reaction mass was refluxed and stirred for 60 min. The reaction mass was cooled and maintained for 180 min. The reaction mass was filtered and washed with acetone. The wet cake was dried in vacuum tray drier at 50-55° C. HPLC Purity>99.5%; Chiral purity>99.31%

Example 9a)

Above reaction was repeated with acetonitrile as solvent. Chiral purity: 99.05%

Example 9b)

Above reaction was repeated with ethyl acetate as solvent. Chiral purity: 98.0%

Example 9c)

20 ml isopropyl alcohol was added to 2 g luliconazole hydrochloride and the reaction mass was refluxed. The reaction mass was cooled, filtered and dried. Chiral purity: 99.27%

Example 9d)

Above reaction was repeated with tetrahydrofuran as solvent. Chiral purity: 99.0%

Example 10: Purification of Luliconazole Hydrochloride in Mixture of Acetone and Water Luliconazole hydrochloride in acetone was heated. To this reaction mixture water was added and maintained at a temperature of about 50-55° C. The reaction mass was cooled, filtered and dried. Chiral purity: 99.82%

Example 11: Preparation of Luliconazole Hydrochloride in Methylene Chloride

A mixture of luliconazole and stereoisomers thereof in methylene dichloride was acidified with hydrochloric acid purged in ethyl acetate. The reaction mass was distilled under vacuum to obtain a mixture of luliconazole hydrochloride and stereoisomers of luliconazole or hydrochloride salts of stereoisomers of luliconazole. Acetone was added to this mixture, stirred and filtered to obtain luliconazole hydrochloride. Chiral purity: 96.87%

The obtained luliconazole hydrochloride was refluxed in methanol for 60 min. Methanol was distilled and to the residue acetone was added, stirred the reaction mass and filtered to obtain luliconazole hydrochloride. Chiral purity: 97.2%

Example 12: Purification of Luliconazole in Mixture of Acetonitrile and Water luliconazole in a mixture of acetonitrile and water was heated to 70-80° C. The reaction mass was then cooled, filtered and dried. Chiral purity: 99.76% HPLC Purity: 99.11%

Example 13: Purification of Luliconazole in Acetone luliconazole is dissolved in acetone and subjected to charcoalisation. The solution is filtered through hyflo bed and the filtrate is removed by distillation to obtain luliconazole Example 14: Purification of Luliconazole Hydrochloride by Acid Base Treatment DM water was added to the luliconazole hydrochloride and basified with 25% aqueous ammonia solution to basic pH. The reaction mixture was extracted with ethyl acetate and washed with water and brine. To the ethyl acetate layer was added a solution of ethyl acetate.HCl and the reaction mixture was distilled to obtain solid. The solid was stirred in acetone, filtered and dried to get Luliconazole hydrochloride. Chiral purity: 98.68%, HPLC Purity>99.5%. Z:isomer content: 0.45%, other undesired isomer content: 0.87%

Example 15: Purification of Luliconazole Hydrochloride in Acetone and Ethyl Acetate HCl Acetone was added to the luliconazole hydrochloride and then added the ethyl acetate.HCl and reaction mass was stirred for 3-4 hours. Luliconazole hydrochloride was filtered and dried washed with acetone get Luliconazole hydrochloride. Chiral purity>95% and HPLC purity>99.0%

Example 16: Purification of Luliconazole in Ethyl Acetate luliconazole was refluxed in ethyl acetate and cooled to 0-5° C. Luliconazole was filtered, washed with hexane and dried. HPLC purity: 99.71%. Chiral purity: 99.94%.

Example 17: Purification of Luliconazole in Mixture of Ethyl Acetate and Hexane

Ethyl acetate was added to luliconazole and the reaction mass was heated to 60-70° C. The reaction mass was cooled and hexane was added. Luliconazole was filtered, washed with hexane to obtain luliconazole. Chiral purity>99.0% and HPLC purity>99.5%

XRD table of luliconazole:

| Pos. [°2Th.] | d-spacing [Å] | Rel. Int. [%] |
|---|---|---|
| 8.09 | 10.92 | 1 |
| 9.8 | 9.02 | 10.55 |
| 12.1 | 7.31 | 24.64 |
| 13.38 | 6.61 | 6.4 |

XRD table of luliconazole:

| Pos. [°2Th.] | d-spacing [Å] | Rel. Int. [%] |
| --- | --- | --- |
| 13.51 | 6.55 | 9.08 |
| 14.60 | 6.06 | 2.81 |
| 16.25 | 5.45 | 41.7 |
| 18.20 | 4.87 | 100 |
| 19.93 | 4.45 | 6.62 |
| 20.57 | 4.31 | 4.8 |
| 21.24 | 4.18 | 34.54 |
| 21.72 | 4.09 | 31.26 |
| 22.14 | 4.01 | 16.82 |
| 22.54 | 3.94 | 3.79 |
| 23.23 | 3.82 | 21.73 |
| 24.38 | 3.65 | 92.5 |
| 24.68 | 3.60 | 7.29 |
| 25.6 | 3.48 | 43.72 |
| 26.9 | 3.30 | 15.46 |
| 27.85 | 3.20 | 13.07 |
| 29.16 | 3.06 | 1.40 |
| 29.6 | 3.01 | 4.55 |
| 29.8 | 2.99 | 6.0 |
| 30.1 | 2.96 | 11.59 |
| 31.23 | 2.86 | 3.77 |
| 32.11 | 2.78 | 1.48 |
| 32.62 | 2.74 | 5.27 |
| 33.4 | 2.68 | 1.39 |
| 33.9 | 2.64 | 1.83 |
| 34.5 | 2.6 | 3 |
| 35.15 | 2.55 | 2.83 |
| 35.65 | 2.51 | 1.32 |
| 37 | 2.43 | 6 |
| 37.3 | 2.41 | 3.15 |
| 38.6 | 2.33 | 3.28 |
| 40 | 2.25 | .99 |
| 41 | 2.2 | 1.69 |
| 41.9 | 2.15 | 1.8 |
| 42.7 | 2.11 | 1.76 |
| 43.35 | 2.08 | 3.1 |
| 44.13 | 2.05 | 3.98 |
| 45.22 | 2.00 | 5.35 |

Example 18: Purification of Luliconazole in Mixture of Ethyl Acetate and Cyclohexane Ethyl acetate was added to luliconazole and reaction mass was heated to 60-70° C. The reaction mass was cooled and cyclohexane was added. Luliconazole was filtered, washed with cyclohexane to obtain luliconazole. Chiral purity>99.0% and HPLC purity>99.5%.

Example 19: Micronization of Luliconazole by Using Jet Mill Under Nitrogen Pressure Luliconazole having a particle size $D_{90}$ of around 300 microns was jet milled with nitrogen pressure 5-7 kg/cm$^3$ to obtain luliconazole with particle size $D_{90}$ below 20 micron.

Comparative Example

To a mixture of 1H-imidazole-1-acetonitrile (compound III) in dimethyl sulphoxide and carbon disulphide was added powered potassium hydroxide to obtain potassium salt of α-(dimercaptomethylene)-1H-Imidazole-1-acetonitrile. In another flask dimethyl sulphoxide and (αS) 2,4-dichloro-α-(chloromethyl)-benzene methanol methanesulfonate (compound V) were added, stirred and cooled. To this reaction mass was added above prepared potassium salt of α-(dimercaptomethylene)-1H-Imidazole-1-acetonitrile. The reaction mass was stirred and quenched in water. The reaction mass was extracted with ethyl acetate and washed with water and brine. The ethyl acetate layer was distilled under vacuum. HPLC purity: 81.61%. Chiral purity by HPLC: Z isomer content: 35.65%, other isomer content: 0.71%

The invention claimed is:

1. A process for the purification of luliconazole, a compound of formula I, comprising the steps of

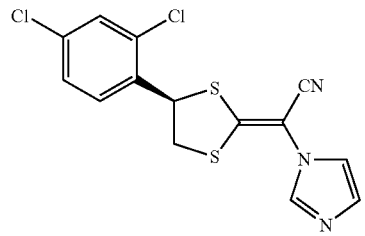

I (i) contacting a mixture comprising luliconazole and stereoisomers thereof in a solvent with an acid to provide a reaction mixture comprising an acid addition salt of luliconazole and an acid addition salt of stereoisomers of luliconazole, wherein the stereoisomers are the Z and SE isomers of luliconazole, the compound of formula VIII and IX respectively;

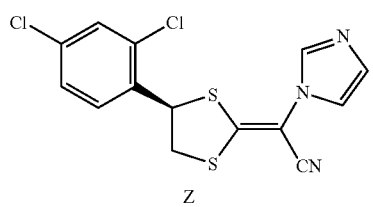

VIII

Z

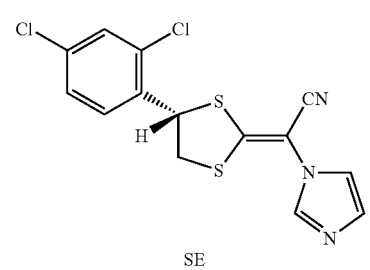

IX

SE (ii) separating the acid addition salt of luliconazole from the reaction mixture, and
(iii) basifying the separated acid addition salt of luliconazole to form luliconazole, wherein
(a) step (ii) comprises:
(Gi) selectively separating the acid addition salt of luliconazole from the reaction mixture, where the reaction mixture comprises the acid addition salt of luliconazole and the acid addition salt of stereoisomer(s) of luliconazole, based on their differential solubility in solvents; and
(Gii) isolating the acid addition salt of luliconazole, and
(b) the acid addition salt of luliconazole is selectively separated by addition of an anti-solvent to the reaction mixture comprising the acid addition salt of luliconazole and the acid addition salt of stereoisomer(s) of luliconazole in a solvent.

2. The process according to claim 1, wherein in step (i) the acid is selected from an organic or an inorganic acid.

3. The process according to claim 2, wherein the inorganic acid is hydrochloric acid.

4. The process according to claim 1, further comprising crystallizing luliconazole from a solvent selected from the group consisting of ketone, nitrile, water, sulfoxides, cyclohexane, and mixtures thereof.

5. A process for the purification of luliconazole, a compound of formula I, comprising the steps of

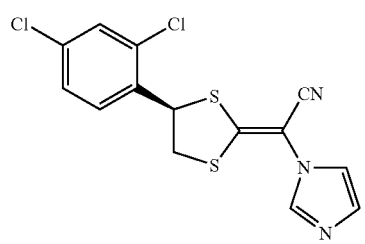

I (i) contacting a mixture comprising luliconazole and stereoisomers thereof in a solvent with an acid to provide a reaction mixture comprising an acid addition salt of luliconazole and an acid addition salt of stereoisomers of luliconazole, wherein the stereoisomers are the Z and SE isomers of luliconazole, the compound of formula VIII and IX respectively;

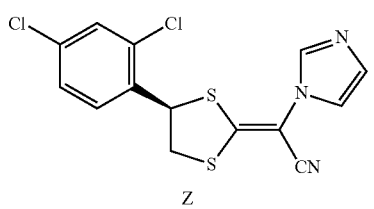

VIII

Z

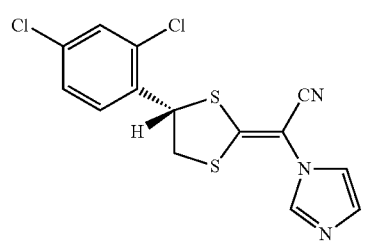

IX

SE (ii) separating the acid addition salt of luliconazole from the reaction mixture, and
(iii) basifying the separated acid addition salt of luliconazole to form luliconazole, wherein
(a) in step (i) the acid is hydrochloric acid; and
(b) the acid addition salt of luliconazole obtained in step (ii) is crystalline luliconazole hydrochloride characterized by an X-ray diffraction (XRD) spectrum having peak reflections at about 4.0, 8.0, 11.9, 15.9 and 17.9±0.2 degrees 2 theta.

6. A process according to claim 5, further comprising

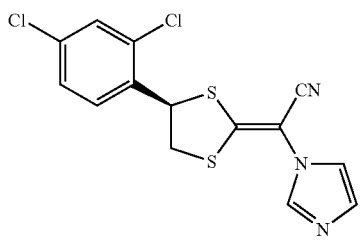

I (iv) isolating the luliconazole, wherein the content of the Z-isomer in the isolated luliconazole is less than 0.5% w/w with respect to luliconazole as measured by HPLC.

7. The process according to claim 6, wherein the content of Z and SE isomer of luliconazole, the compound of formula VIII and IX respectively, in the obtained luliconazole is less than 0.5% w/w with respect to luliconazole as measured by HPLC.

8. A process for the purification of luliconazole, a compound of formula I,

I the process comprising:
(ii) contacting a mixture comprising luliconazole and stereoisomers thereof in a solvent with hydrochloric acid to provide a reaction mixture comprising luliconazole hydrochloride and any stereoisomers of luliconazole, wherein the stereoisomers are the Z and SE isomers of luliconazole, the compound of formula VIII and IX respectively

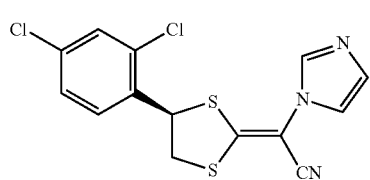

VIII

Z

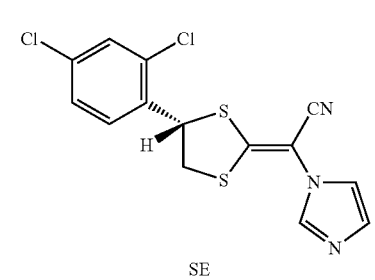

IX

SE (ii) separating the luliconazole hydrochloride from the reaction mixture of step (ii); and
(iii) basifying the separated luliconazole hydrochloride to form luliconazole,
wherein the luliconazole hydrochloride obtained in step (ii) is crystalline luliconazole hydrochloride characterized by an X-ray diffraction (XRD) spectrum having peak reflections at about 4.0, 8.0, 11.9, 15.9 and 17.9±0 0.2 degrees 2 theta.

9. The process according to claim 8, wherein the content of Z and SE isomer of luliconazole in the obtained luliconazole is less than 0.5% w/w with respect to luliconazole as measured by HPLC.

* * * * *